(12) United States Patent
Menkara (10) Patent No.: US 10,908,074 B1
(45) Date of Patent: Feb. 2, 2021

(54) SYSTEM AND METHOD FOR FLY ASH ADSORPTION CAPACITY DETERMINATION

(71) Applicant: Hisham Menkara, Kennesaw, GA (US)

(72) Inventor: Hisham Menkara, Kennesaw, GA (US)

( * ) Notice: Subject to any disclaimer, the term of this patent is extended or adjusted under 35 U.S.C. 154(b) by 0 days.

(21) Appl. No.: 16/873,302

(22) Filed: Mar. 14, 2020

Related U.S. Application Data

(60) Provisional application No. 62/919,556, filed on Mar. 18, 2019.

(51) Int. Cl.
*G01N 21/25* (2006.01)
*G01N 35/10* (2006.01)

(52) U.S. Cl.
CPC ....... *G01N 21/255* (2013.01); *G01N 35/1009* (2013.01)

(58) Field of Classification Search
CPC .................. G01N 21/255; G01N 35/1009
USPC .................................. 356/432–444
See application file for complete search history.

(56) References Cited

U.S. PATENT DOCUMENTS

| | | | |
|---|---|---|---|
| 4,453,978 A | 6/1984 | Okimura et al. | 108/661 |
| 5,286,292 A | 2/1994 | Tsukada et al. | 106/705 |
| 6,706,111 B1 | 3/2004 | Young | 108/705 |
| 9,045,366 B2 | 8/2015 | Brien | |
| 9,527,772 B2 | 12/2016 | Georges et al. | |
| 9,651,497 B2 | 3/2017 | Minkara et al. | |
| 2012/0304893 A1 | 12/2012 | Georges et al. | 106/677 |
| 2013/0019779 A1 | 1/2013 | Georges et al. | 106/708 |

FOREIGN PATENT DOCUMENTS

WO WO 2015/054556 A1 4/2015

*Primary Examiner* — Tri T Ton
(74) *Attorney, Agent, or Firm* — Chris Whewell (57) ABSTRACT

Provided are systems and methods for determining physical properties of solids in solution or suspension. In some embodiments, the present methods employ absorbance for determining the amount of a first material which is adsorbed by a second material when the two are made to contact one another. Through use of the present system and methods it is possible to accurately determine the amount of an air entraining agent which is adsorbed by a particular lot of a fly ash material used in the production of cements and concretes. Use of the technology disclosed herein eliminates errors in formulation of cements and prevents large amounts of waste concrete being generated using prior art methods, which translates to significant savings of resources, both material and financial.

17 Claims, 8 Drawing Sheets

SYSTEM AND METHOD FOR FLY ASH ADSORPTION CAPACITY DETERMINATION

This invention was made with government support under contract DTRT5717C10191 awarded by the United States Federal Highway Administration, Department of Transportation. The government has certain rights in the invention.

TECHNICAL FIELD

This invention relates to systems and methods for determining the adsorption capacity of fly ash materials intended for use in the manufacture of concrete. Methods for measurement of physical properties of materials present in a various fluid substances are disclosed.

BACKGROUND OF THE INVENTION

The statements in this background section merely provide background information related to the present disclosure and may not constitute prior art.

The electrical generation industry produces hundreds of tons annually of a waste material that is commonly termed "fly ash". Fly ash is well-known to be a particulate solid resulting from the combustion process at power plants which burn carbon or hydrocarbon feedstocks as fuel. Thus, fly ash is generally regarded as a waste product; however, in the past it has been found that the material makes a beneficial value-added product for inclusion in concrete formulations, being used in the place of a portion of the Portland cement component of concretes, and some grouts.

One reason that fly ash is desirably added to concrete compositions is due to its ability to stabilize micro air bubbles which are further stabilized by the presence of an added air-entraining agent (AEA). AEA's are often selected to be surfactants, and when adsorbed onto fly ash in a concrete formulation, the AEA's enable stabilization of tiny bubbles of air introduced during the mixing step of the concrete production process. This results in cured concrete formed from such fly-ash and AEA containing cements having a significant amount of air entrained within the finished concrete. The presence of such entrained air bubbles adds significantly to the performance of the concrete, especially in climates where the concrete is subjected to thermal cycles including repeated freezing and thawing, since the tiny air bubbles can expand and contract with the changes of temperature, and function effectively as an internal "shock absorber" which reduces stresses throughout the bulk of the cured concrete. The observed result by hundreds of persons of ordinary skill in this art over the past several decades, is that concrete formulated with fly ash and an appropriate type and amount of AEA does not crack when present in climates subject to repeated freeze-thaw cycles, particularly those regions above about the $25^{th}$ parallel of the globe. Increased service life of concrete underlayments including without limitation dwelling foundations and highways translates to significant cost savings to civil governments, businesses, and private citizens alike.

However, due to variations in the chemical make up of fly ash derived from different sources, such as different coal-fired power plant, the proposition is not a straight-forward one whereby a plant operator can merely add an AEA to fly ash on a weight percentage basis and then make a high-performance cement from it. It has been found that fly ashes from different sources have varying inherent abilities to adsorb a particular selected AEA onto their surfaces, thereby increasing the requirement for more AEA to be added to the fly ash, due to the AEA lost to adsorption. This is sometimes true also from even the fly ash from a single source, depending upon combustion parameters, feedstock qualities, moisture, ambient temperature, and other typical factors.

It has been problematic in this art for formulators of concrete using fly ash and an AEA as ingredients in cement, to determine the correct amount of AEA to use or add to a particular batch of fly ash. When an inappropriate amount of AEA is added to fly ash, the desirable freeze-thaw thermal cycling protection against cracking of the concrete is forfeit. This has occurred many many times in the past, resulting in costly breaches of contract suits, and inconveniences costing in aggregate in the billions of dollars.

To address the question of what proper amount of AEA to add to a batch of fly ash, workers in the past developed bench tests, including a foam test. Known tests employ addition of an AEA in various amounts in different aliquots to a fly ash suspension with a surfactant present, and the optimally-foaming test aliquot is singled out as representing a desirable addition amount. While providing some correlation between added AEA and the adsorption capacity of a particular lot or batch of fly ash, the subjective foam tests are recognized to possess significant shortcomings.

Other methods workers in the past have employed when attempting to determine a correct amount of AEA to add to a batch of fly ash involve spectroscopy, such as spectroscopy involving fluorescence or absorbance after addition of an acid-base indicator to a batch of fly ash. Along these schemes, the indicator called methylene blue has been a popular choice for decades. Essentially, a solution of methylene blue in a known concentration is digested or steeped with a known quantity of fly ash, and a change in fluorescence of the solution after passage of a known quantity of time is correlated to the adsorptive capacity of the particular batch of fly ash tested.

Yet, as with the foam-test methods, fluorescence spectroscopy methods involving fly ash and surfactant mixtures, and absorbance spectroscopy methods involving methylene blue and fly ash have up to this time not provided consistent, accurate correlation between the adsorption capacity of a given lot or batch of fly ash, and a measurable analytical quantity or signal that one might expect, given the state of the art of analytical techniques. Particularly, the adsorption kinetics of methylene blue on carbon in fly ash differ from those of surfactants and AEA's. That makes the methylene blue method often unreliable in accurately predicting AEA adsorption capacity. Moreover, substances like methylene blue require special handling and pose unique issues for waste treatment systems.

SUMMARY OF THE INVENTION

Provided is a robust and semi-automated spectroscopy system and methods having a broad UV/VIS spectral range, capable of measuring adsorption capacity of any combination of fly ash and air-entraining agents. The system and methods can rapidly and accurately identify and measure different AEA surfactants, and quantify the amount of a selected surfactant which any particular lot or batch of fly ash adsorbs. Systems according to some alternate embodiments employ modified methods, emission sources, and sensors that enable precise and accurate measurement of a wide range of optical, electrical, and physical properties of materials present in fluids.

BRIEF DESCRIPTION OF THE DRAWINGS

The drawings shown and described herein are provided for illustration purposes only and are exemplary of features of different embodiments and not intended to be construed in a delimitive fashion.

DETAILED DESCRIPTION

The following description is exemplary in nature, and is not intended to limit the present disclosure, application, or uses.

Figure 1:
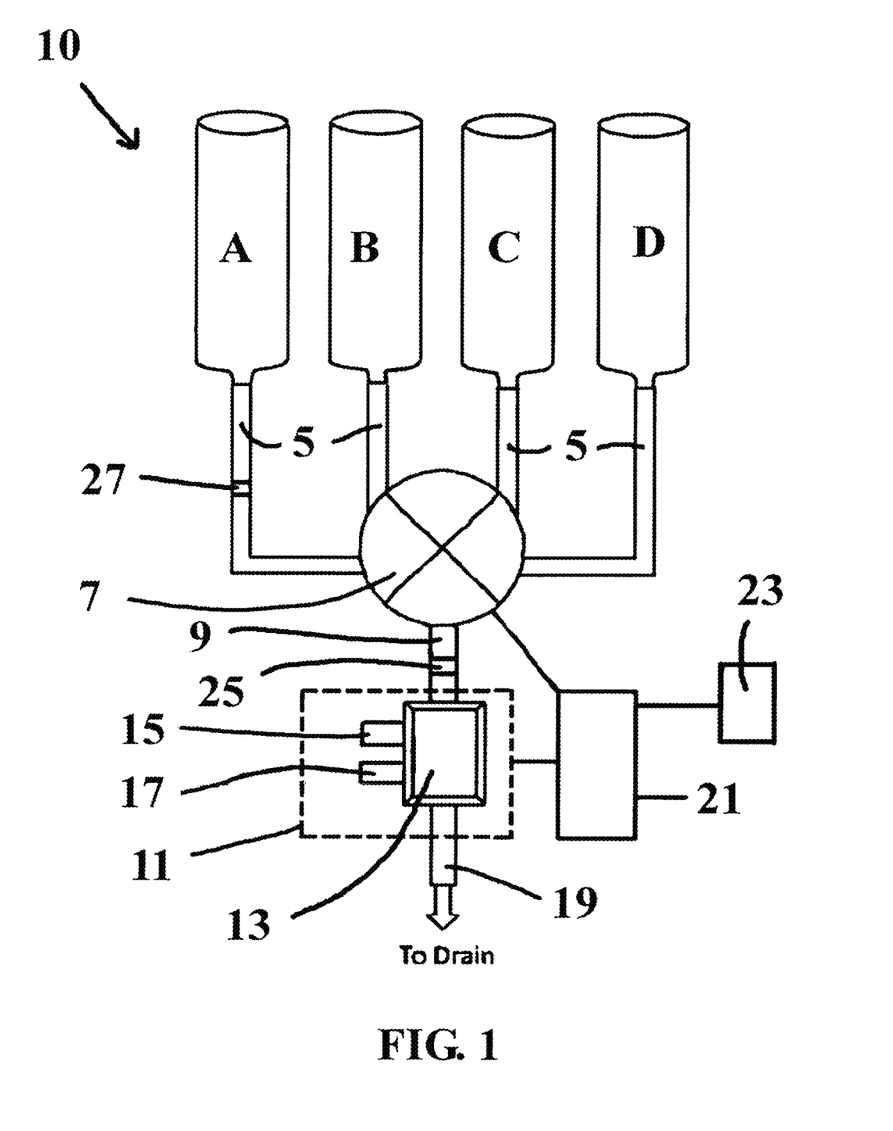
FIG. 1 is a schematic view of a system useful in accordance with some embodiments of the disclosure.

Referring now to the drawings, and initially to FIG. 1, there is shown a schematic illustration of an exemplary system 10 useful in accordance with some embodiments of the instant technology. The system of FIG. 1 includes a plurality of solution reservoirs, labeled as A, B, C, D, each of which are provided to be in fluid communication with inlet ports present on a selectively-actuable switching valve 7, by means of conduits 5. Switching valve 7 can be any conventional multi-ported valve, either electrically-actuated, pneumatically-actuated or actuated otherwise, having a plurality of input ports, and an output port such as that to which transfer conduit 9 is in fluid communication with. One non-limiting suitable example is valve model number EPC6W from VICI Valco Instruments company of Houston, Tex. Any type of selectively-actuable valve is suitable, provided it is capable of selectively exclusively passing only a fluid derived from a single reservoir either A, B, C, D at any selected time interval, to transfer conduit 9 at its outlet port. In some embodiments, reservoirs A, B, C, D contain aqueous solutions or suspensions; however, other solvents are suitable, including organic solvents. These reservoirs also can be considered in some embodiments as being dispensers.

Transfer conduit 9 is configured to deliver fluid to sensing module 11, which itself comprises a test cavity 13, an energy source 15, and a detector 17. There is an effluent conduit 19 attached to the outlet of sensing module 11, which is directed to a drain and collected as waste solution. Microprocessor 21 is shown, being in effective electronic communication with both the switching valve 7 and sensing module 11. Microprocessor 21 is able to send and receive data to and from switching valve 7 and module 11, and to control the position of switching valve 7.

Test cavity 13 can be considered as a zone within a continuous fluid conduit leading from transfer conduit 9 to effluent conduit 19. In some embodiments, the shape and configuration of the conduit present within test cavity 13 is tubular. In other embodiments, the shape and configuration of the conduit present within test cavity 13 is cubic. In further alternate embodiments, the shape and configuration of the conduit present within test cavity 13 is substantially-planar. Regardless of the geometry selected for test cavity 13, it is essential that both energy source 15 and detector 17 be in substantial proximity to at least a portion of test cavity 13, sufficiently to enable detector 17 to detect a signal emitted from energy source 15 after such energy emitted from energy source 15 has passed through a definite portion of the solution present in test cavity 13. In some embodiments, test cavity 13 is tubular in shape and detector 17 is disposed on one side of such tubing, and energy source 15 is disposed on the opposite side of such tubular test cavity 13. In some embodiments, test cavity 13 comprises a glass flow cuvette. Test cavity 13 can be comprised of any material selected from the group consisting of: glass, quartz, any selected polymer or polymer blends, silicone, metals and metallic alloys. When solutions are mentioned in this disclosure, this is also intended to be applicable as including suspensions, depending on context.

Energy source 15 can be any selected source of electromagnetic radiation, including without limitation those which emit infrared light frequencies, visible light frequencies, and ultraviolet light frequencies. In some embodiments energy source 15 is selected as being a source which emits microwaves. In other embodiments energy source 15 is selected as being a source which emits ultrasonic waves. In other embodiments, energy source 15 is selected as being a source which emits electrons, or an electrical current which can be a pulsed DC-current, or an alternating current of any selected frequency.

Detector 17 is selected as being a transducer capable of outputting a signal responsive to frequencies emitted by energy source 15. That is, when energy source 15 is selected to be a source of UV/VIS radiation, detector 17 is selected as being a UV/VIS detector. When energy source 15 is selected to be a source of microwave radiation, detector 17 is selected as being a microwave detector, etc. Detector 17 in various embodiments can be selected from optical, electrical, acoustic, or mechanical sensors which output a voltage signal responsive to energy provided by energy source 15.

In some embodiments microcontroller 21 is in effective electrical communication with switching valve 7 and sensing module 11. This communication involves microprocessor 21 having a plurality of inputs, and a plurality of outputs sufficient in some embodiments to control energization of energy source 15, gather data from detector 17, and issue commands to switching valve 7 concerning which reservoir of A, B, C, D a solution is selected to be directed to transfer conduit 9 at any selected time. In some embodiments, solutions from reservoirs A, B, C, D are fed to switching valve 7 by gravity flow. In other embodiments, solutions from reservoirs A, B, C, D are fed to switching valve 7 by means of pumps disposed along conduits 5, which can be peristaltic pumps. Microcontroller 21 is selected to be a programmable microcontroller and can accordingly be any microprocessor or microcontroller that is able to be programmed to carry out the steps necessary for making determinations as set forth herein, including communicating with a software code. In general, most microcontrollers having a USB or serial interface are suitable. One non-limiting example of a suitable microprocessor is model number TUSB 3410 made by Texas Instruments Corporation of Dallas, Tex. Computer-readable memory 23 is present, in effective electrical communication with microcontroller 21, and in some embodiments is employed externally as part of a hand-held device such as a smartphone, a laptop computer, a desktop computer, or like device. Absorbance and any other data provided by detector 17 is stored in memory 23 for subsequent retrieval and use in calculations, such as to provide absorbance curves and correlation of spectral data to concentration of a selected substance present in samples analyzed. Memory 23 can be any conventional computer memory which can be written to, and read by, a microprocessor including without limitation RAM memory.

Although the embodiments set forth schematically in FIG. 1 are depicted as comprising four solution reservoirs A, B, C, D, the present technology is not limited in the number of reservoirs or sources of solutions which can be employed during analytical determinations. A requisite for expansion is merely to re-configure switching valve 7 as having a number of inputs corresponding to the number of solution reservoirs employed. Alternately, four reservoirs can be employed, and the reservoirs rinsed adequately prior to adding a different material than it previously contained.

In some embodiments, at least one of filters 25, 27 are selected to be present, either in line of conduits 5 and alternately in transfer conduit 9. In some embodiments, these filters, wherever they are selected to be present, may comprise membrane filters capable of filtering solid particulates from a solution prior to the analyte being conveyed to sensing module 11. Employment of such a filter ensures in some embodiments that the analyte is free from solid particles when impinged on light or other energy from energy source 15.

In some embodiments employing a method according to the disclosure, the exact equipment configuration can vary and it is possible to employ only a single solution reservoir, wherein the solution reservoir comprises a syringe, and the filter 27 is of the type which screws on the end of a syringe, such as a Leuer lock syringe. In some embodiments, a hydrophilic membrane is employed as the filter. In some embodiments, polyether sulfone membrane is employed. Membrane filters having a nominal size of 33 mm are suitable, but in general the filter is selected to not permit any particles larger than about 0.30 microns to enter sensing module 11.

In some embodiments, one of the solution reservoirs present can be selected to contain a pure solvent absent any solute, from which solute the remaining solutions are made to include. This enables a rinsing cycle or period to be programmed, to flush test cavity 13 of its contents from a previous determination. In some embodiments, the solvent employed is purified water, however any solvent may be used depending on the determination being made, further including alcohols, ketones, hydrocarbons, halocarbons, ethers, esters, mixtures thereof, aqueous mixtures thereof, and generally any material that is recognized as being a suitable solvent for a particular solute selected to be analyzed. In addition to solutions, the present technology also employs suspensions in some determinations. In addition to solutions and suspensions, some embodiments of the present technology employ colloids in some determinations. The following examples are illustrative:

Example I

Figure 2:
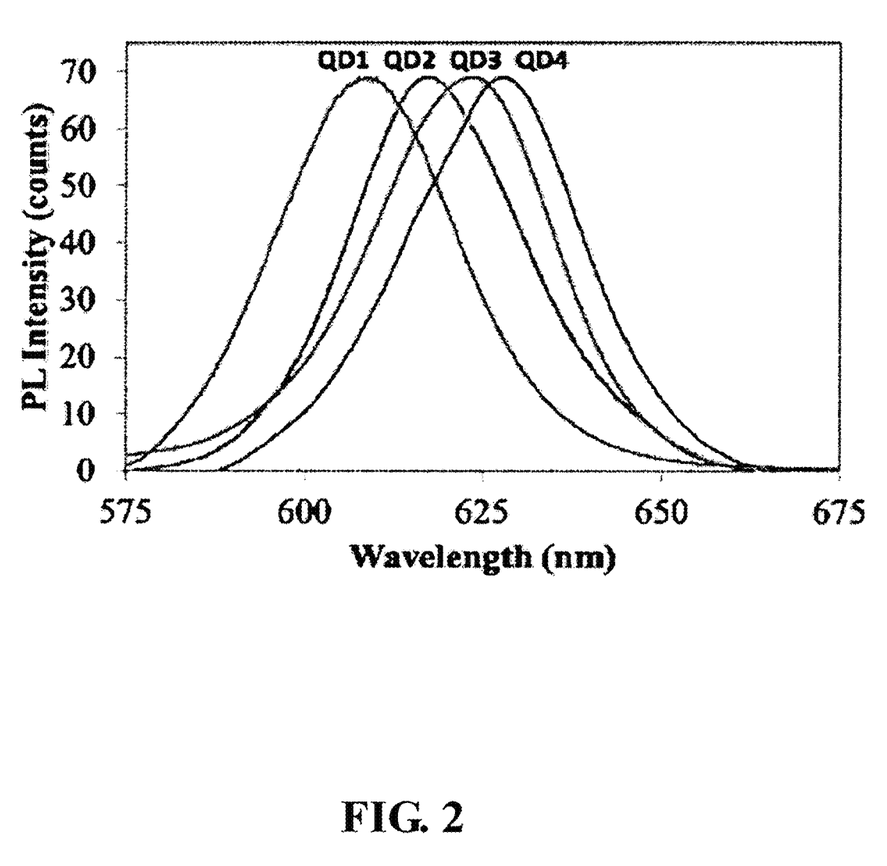
FIG. 2 is the spectral emission/color data obtained using four different quantum dot liquid samples excited by a light source emitting at 450 nanometers (nm)

Four different quantum dot (QD) solutions are prepared using QD materials suspended in a solvent comprising toluene at concentrations below 0.1% by weight based on the total weight of each suspension. Each suspension is made up to contain QDs having different core particle sizes, which produce emission in the wavelength range of between 600 nm and 650 nm. The four different suspensions are introduced into four reservoirs as depicted in FIG. 1 and sequentially routed into a glass flow cuvette, via switching valve 7. An LED light source emitting 450 nm light is selected as energy source 15, and is disposed within test cavity 13 to illuminate one side of the cuvette. A fiber optic cable is disposed to receive the partially transmitted blue light along with the photoluminescence from the QD material for the suspension from each of the reservoirs at different selected times. The fiber optic cable delivers the light to a VIS/NIR spectrometer, such as model number HR 2000 made by Ocean Optics Company of Largo, Fla., which processes the light, thereby providing a set of resulting QD spectral data, which are depicted in FIG. 2.

Example II

Figure 3:
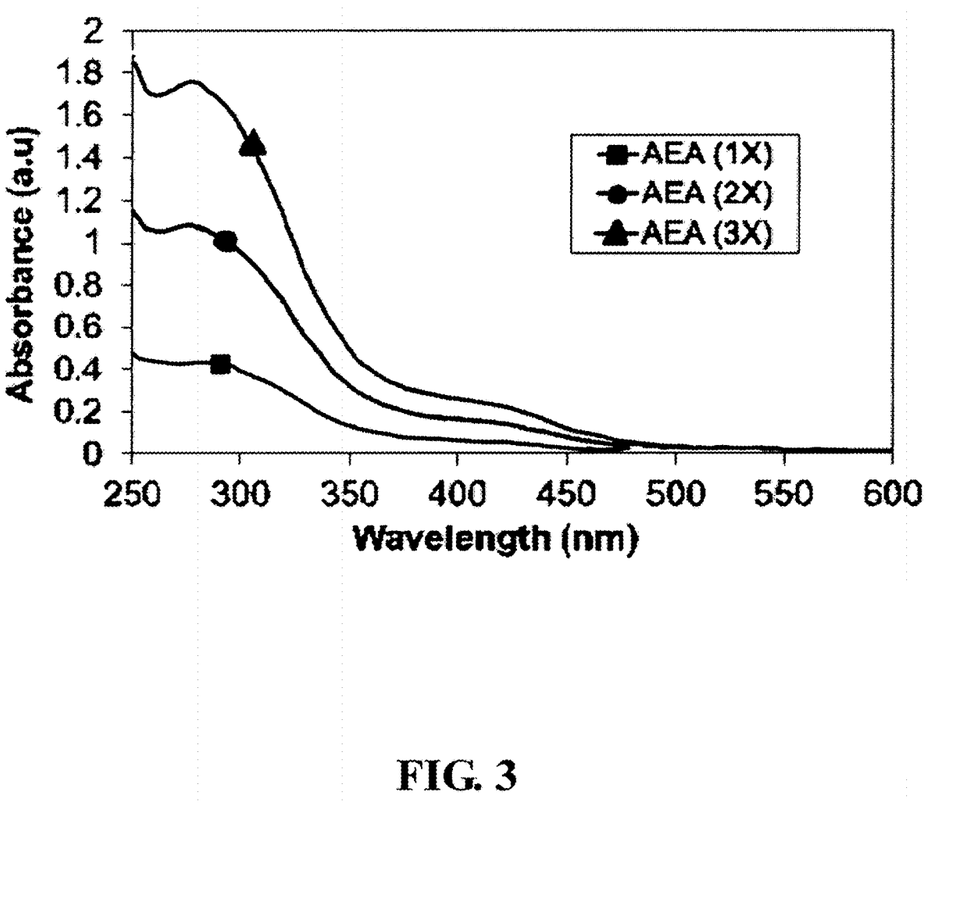
FIG. 3 is a graphical representation of absorbance versus wavelength from three different aqueous samples having increasing AEA concentration relative to a water reference.
Figure 4:
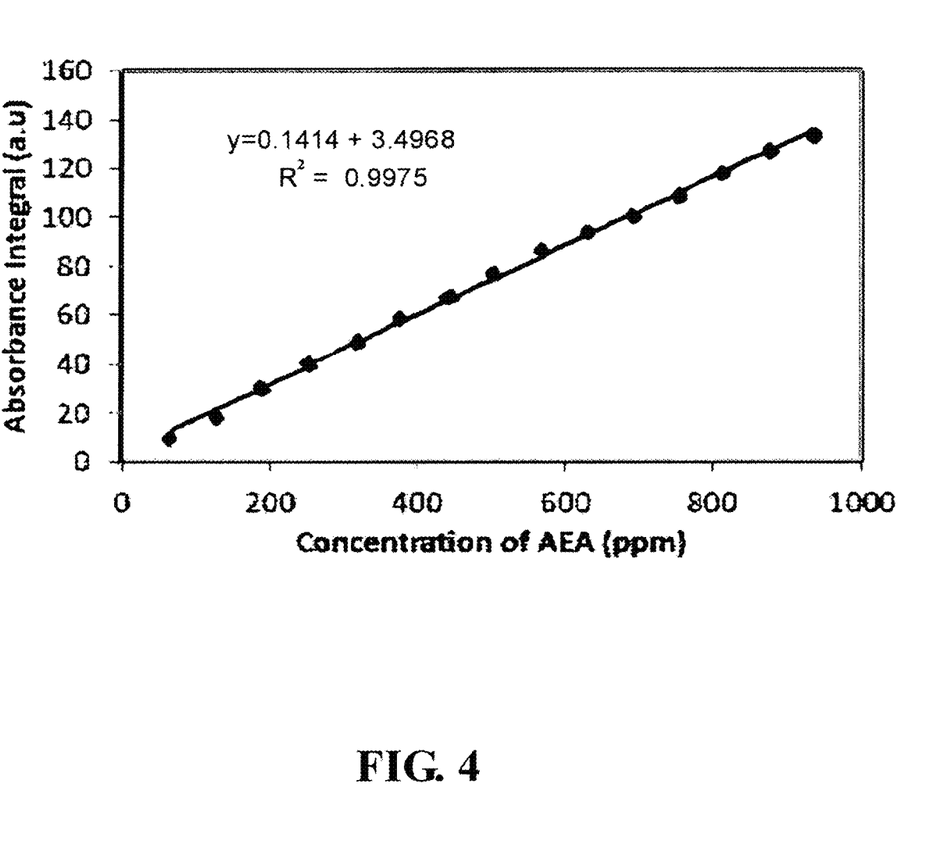
FIG. 4 is a graphical plot of the absorbance integral versus concentration of an AEA derived from aqueous AEA samples of varied concentration relative to a water reference.

A concentrated air-entraining agent (AEA) is diluted in triple-distilled water to various selected concentrations between 64 parts per million by weight (ppm) and 940 ppm, based on the total weight of the solution. The diluted AEA solutions are then introduced into 15 different reservoirs (Reservoirs #1 to #15) with one reservoir (Reservoir #16) containing only triple-distilled water. The water only sample reservoir is used as an absorbance reference sample to which data generated based on the remaining AEA-containing samples (Reservoirs #1 to #15) are compared. The microprocessor is programmed to command switching valve 7 to cause about 20 ml of water (from Reservoir #16) to be passed into or through a quartz cavity (a 2 centimeter long flow cuvette), as a flush. The flow cuvette is disposed between a detector 17 comprising a UV/VIS spectrometer, and a UV/VIS lamp as energy source 15. The absorbance spectrum from the water-only present in Reservoir #16 is collected and stored in computer-readable memory 23 in effective communication with microprocessor 21, which is also employed to store typical data associated with the operation of a microprocessor, including software instructions. Subsequently, microprocessor 21 commands switching valve 7 to sequentially switch its input flows beginning with Reservoir #1 and including all reservoirs up to Reservoir #15, permitting about 20 ml from each dispenser through the flow cuvette. When switching valve 7 switches to a particular dispenser position, microprocessor 21 collects and stores the UV/VIS absorbance spectrum from each particular sample in memory 23. In some embodiments, the rinse from reservoir #16 is provided to the cuvette inbetween the collection of data from analyzing the samples. The spectral absorbance data is then processed using a software or a spreadsheet, and can be graphed and compared using conventional techniques (FIG. 3). The absorbance data from each sample is subsequently correlated to the AEA concentration present in each sample from each reservoir. A curve fit of the data can then be used to measure and predict the AEA concentration of any unknown sample(s) (FIG. 4).

The present technology is suited for measuring absorbance of different AEA's over a range of concentrations. In some embodiments, system 10 is programmed to alternately measure absorbance from a sample analyte and a reference solution. In some embodiments, the light intensity measured for the reference is subtracted from the light intensity measured for the sample analyte. In this fashion, greater accuracy and precision of results is obtained compared to when proceeding using prior art methods. By employing a plurality of samples in a plurality of reservoirs and automating the process by software instructions, absorption profiles of various AEA's are readily generated and stored in memory 23. These data then yield by simple calculation the concentration of a given AEA solution merely by measuring its absorbance. Then, the difference in absorbance values of an AEA solution measured prior to, and after addition of a particular fly ash sample can be used to calculate the adsorption capacity of the fly ash. Knowing this, the formulator of a cement composition is then assured of knowing the correct amount of fly ash from a particular batch or lot to add to a batch of concrete being prepared. Through use of the instant technology, wasted batches of inferior concrete are all but eliminated.

In another illustrative example, an alpha-olefin sulfonate surfactant was selected as the AEA, and the solution employed was water. Several solutions of the sulfonate surfactant in water were prepared, in the concentration range of between 70.4 ppm and 1037.7 ppm. It was found that the absorbance data of the sulfonate surfactant in the range of 210 nanometers to 330 nanometers exhibits good linearity with changes of concentration in the range selected. A linear fit between concentration and absorbance was obtained, and the data are presented in Table I below:

TABLE I

Alpha-olefin sulfonate AEA

| AEA Volume (milliliters) | Solution Volume (milliliters) | Concentration (ppm) | Absorbance Integral (a.u) |
|---|---|---|---|
| 0.052810075 | 786 | 67 | 5.4884 |
| 0.105485945 | 787 | 134 | 8.2921 |
| 0.158028119 | 788 | 201 | 13.95065 |
| 0.210437106 | 789 | 267 | 15.29895 |
| 0.262713413 | 79 | 333 | 16.66965 |
| 0.314857541 | 791 | 398 | 22.2207 |
| 0.366869993 | 792 | 463 | 22.17645 |
| 0.418751265 | 793 | 528 | 27.84985 |
| 0.470501855 | 794 | 593 | 27.84985 |
| 0.522122254 | 795 | 657 | 33.32375 |
| 0.573612954 | 796 | 721 | 36.14975 |
| 0.624974442 | 797 | 784 | 37.5089 |
| 0.676207205 | 798 | 847 | 41.78255 |
| 0.727311726 | 799 | 910 | 44.52675 |
| 0.778288485 | 800 | 973 | 48.7785 |

Figure 5:
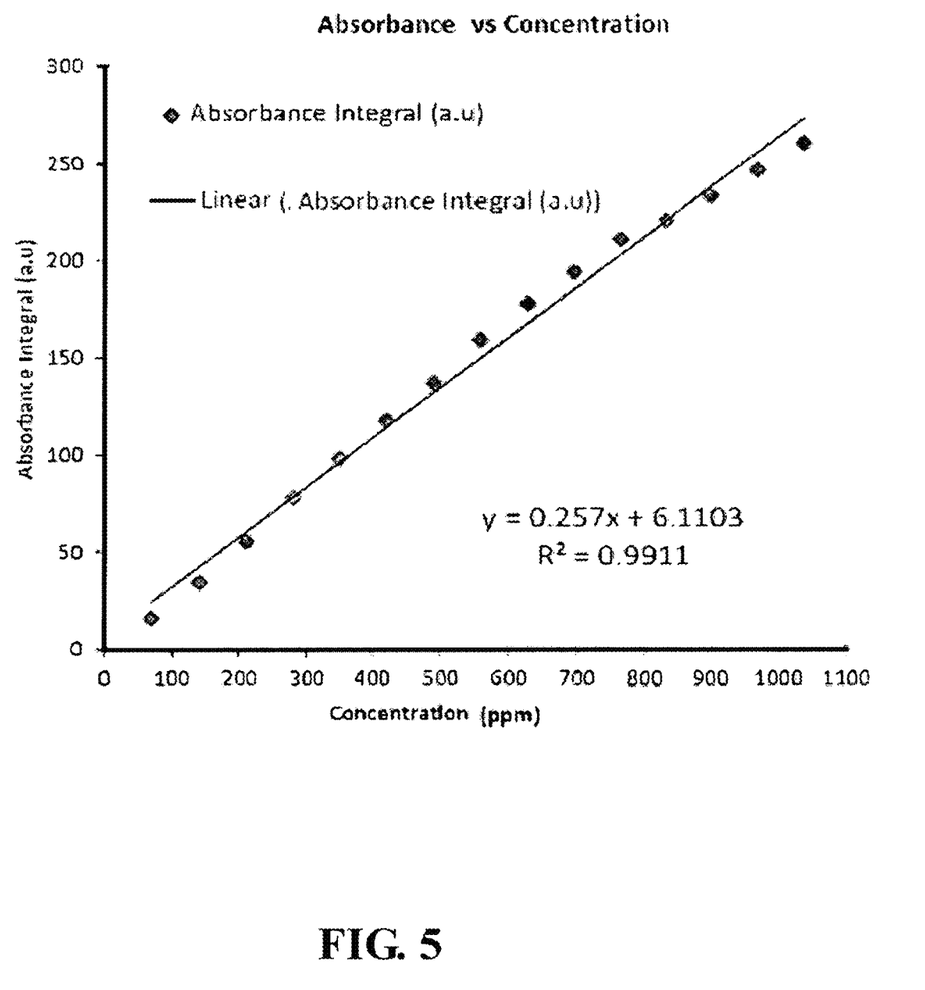
FIG. 5 is a graphical illustration of the absorbance integral versus concentration of an alpha-olefin sulfonate surfactant AEA obtained from aqueous samples of varied AEA concentration relative to a water reference.

These data are depicted graphically in FIG. 5. In order to test viability of the system a first person made up a solution of the alpha-olefin sulfonate surfactant in water and provided it to a second person to analyze without informing the second person of the concentration of the sulfonate surfactant. The second person analyzed the sample using system 10, and from the absorbance data in Table I and FIG. 5, the concentration of the sulfonate surfactant was determined by the second person with an error of only 1.90%.

The foregoing procedure for generating the graphs of FIG. 4 and FIG. 5 can be employed to generate analogous data for any selected surfactant that is desired to be used as an AEA, and by generating such data for a plurality of surfactants, a library of absorbance/transmittance or other data can be generated and maintained within memory 23.

Figure 6:
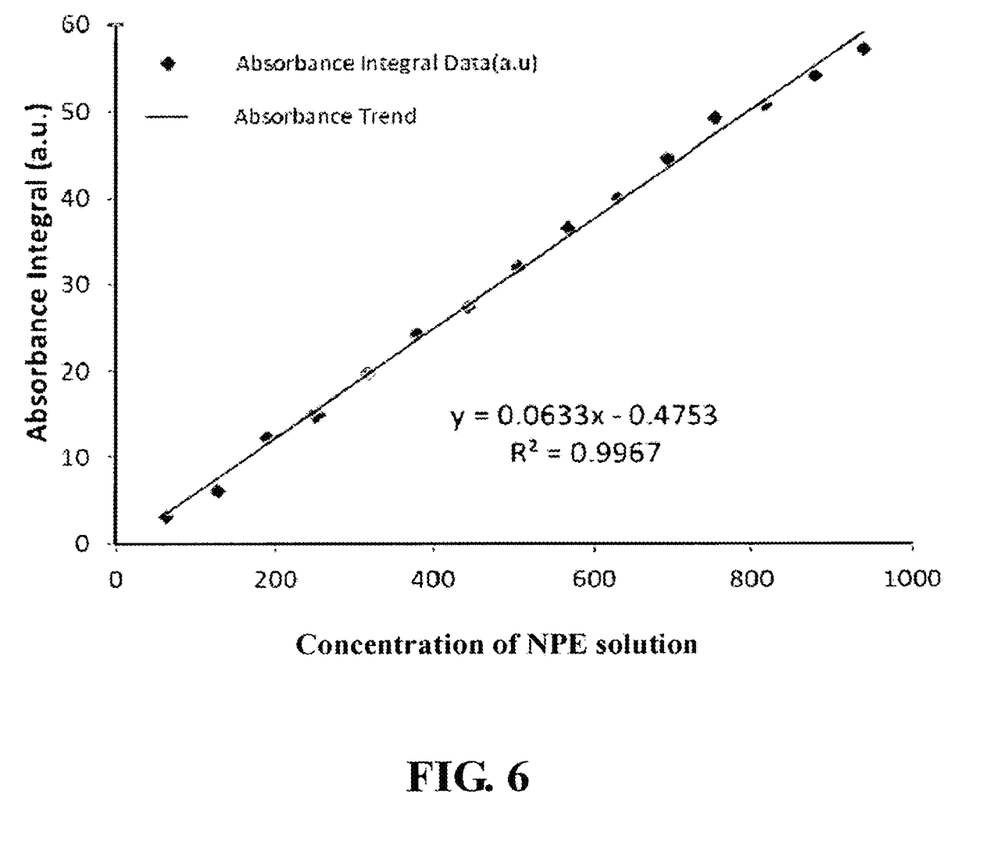
FIG. 6 is a graphical illustration of the absorbance integral versus concentration of a nonyl-phenol ethoxylate ("NPE") surfactant AEA obtained from aqueous samples of varied NPE content relative to a water reference.
Figure 7:
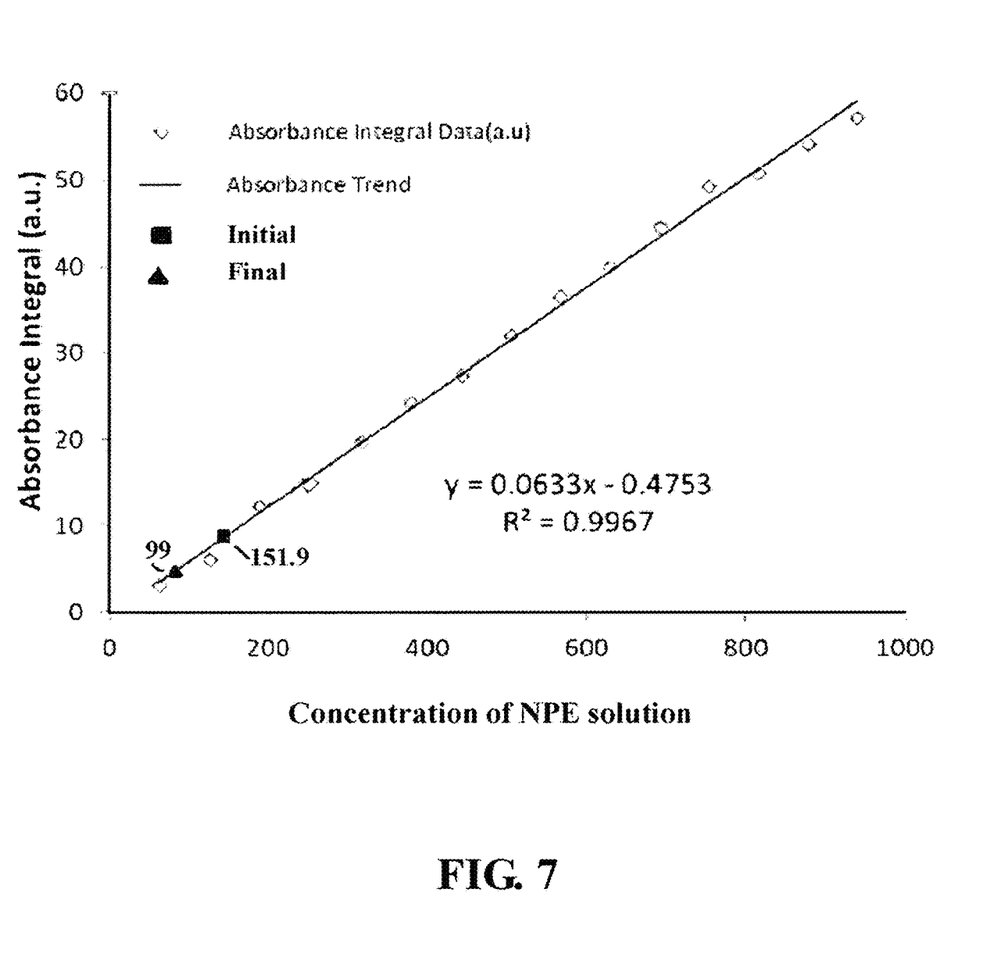
FIG. 7 is a graphical illustration of the absorbance integral versus concentration of a nonyl-phenol ethoxylate surfactant AEA obtained from aqueous samples of varied NPE concentration relative to a water reference, also depicting two analyte data points.

In another illustrative operation, several solutions of a nonylphenol ethoxylate ("NPE") surfactant in water were prepared at varying concentrations and analyzed by the system 10 using a light source emitting at the wavelength of 190 nanometers to 900 nanometers. FIG. 6 shows the absorbance integral versus concentration obtained. Next, a sample of 151.9 parts per million of NPE in water was prepared, and mixed with a fly ash sample from Boral Limited company, fly ash product #1223. The mixture was stirred for ten minutes and permitted to rest for 15 minutes to permit sedimentation of the fly ash. During this time, some of the NPE surfactant had become adsorbed onto the fly ash. A determination was made using absorbance has herein outlined, prior to addition of fly ash #1223, and after sedimentation. The difference in absorbance values before addition of the fly ash to the surfactant solution and after the sedimentation occurred is depicted in FIG. 7. From this it was determined that the concentration of NPE in the solution had decreased from 151.9 ppm to 99 ppm. Accordingly, the adsorption capacity of the particular lot of Boral fly ash product #1223 used was determined to be 1.10 milligrams per gram of the NPE surfactant AEA, based on the original sample weight. Thus, when making a concrete composition using the particular lot of Boral fly ash product #1223 selected, the formulator will add an extra 1.10 milligrams of the NPE surfactant above the normal amount they would otherwise have employed using prior art test methods, to compensate for the amount that was adsorbed on the fly ash.

In some embodiments, a plurality of data plots such as that in FIG. 6 are generated for each of a plurality of surfactants, using the LINEST® program within the Microsoft Corporation's EXCEL® product. These plurality of data are stored in memory and it is possible later, to identify a particular surfactant solution merely by analyzing it for absorbance as outlined herein at different concentrations using simple comparison software. This capability advantageously enables identification of which surfactant is present in a particular selected solution.

In some embodiments, system 10 is employed with pure water present in reservoirs B, D. Sensing module 11 is connected directly to a PC computer via its USB port, and the microprocessor and memory of the PC are employed in the stead of microprocessor 21 and memory 23. Control of switching valve 7 and commands for energy source 15 and data acquisition via detector 17 are fed directly into the PC for processing.

Figure 8:
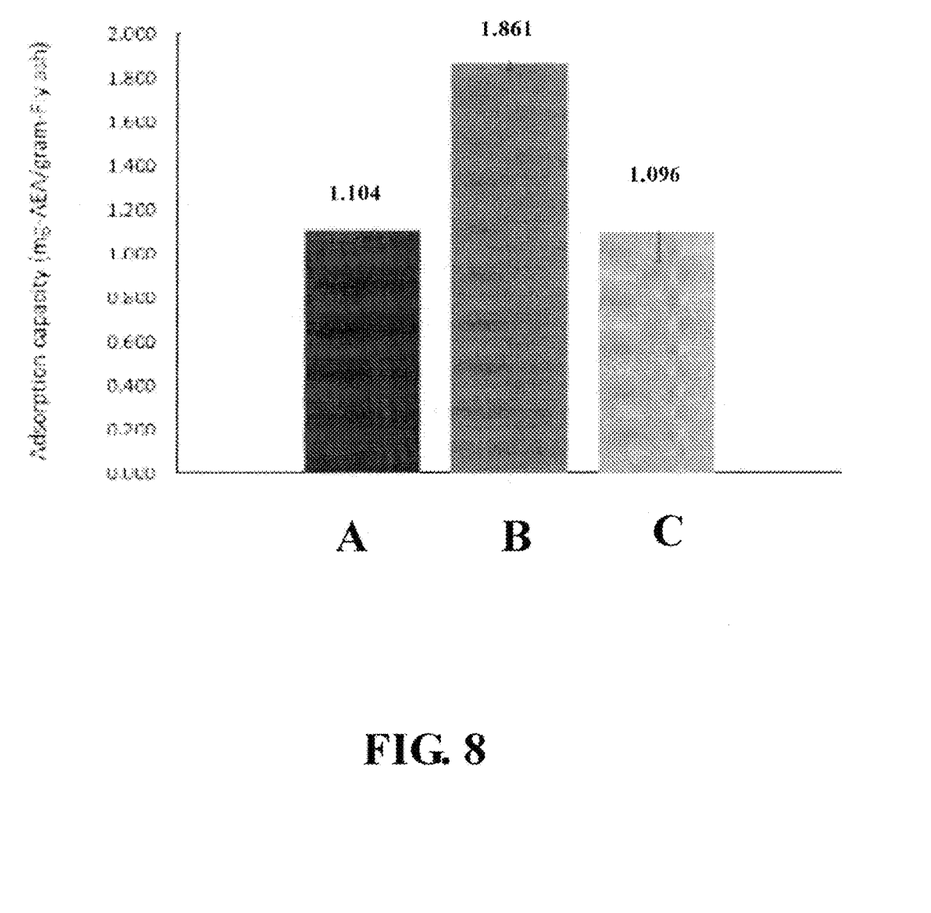
FIG. 8 is a bar graph depicting the amount of AEA surfactant adsorbed on different fly ash samples using different AEA's

In FIG. 8 are depicted three bar graphs, each of which are the result of three different adsorption capacity test routines for a fly ash sample. Bar A employed AEA #1 with a fly ash sample #1, bar B employed AEA #2 with a fly ash sample #1, and bar C employed AEA #3 with a fly ash sample #2. The values of adsorption capacity for each of the surfactants with the fly ash sample were determined as before and are depicted in milligrams of AEA surfactant per gram of fly ash. Thus, the versatility of the instant system is illustrated, since the person of ordinary skill readily recognizes its new ability to generate data for any fly ash sample, using any selected AEA material. In like fashion, using a single surfactant AEA, and employing many different fly ash samples, a multi-bar graph representing the adsorption capacity of a plurality of fly ash samples with respect to a single AEA can be generated.

In order to effectuate the afore-described analyses, reservoir A of FIG. 1 is caused to contain a solvent only, which is often water. Running the spectrum of the solvent provides a background signal, that is later to be subtracted from the absorbance data derived from running the spectra on the contents of reservoirs B, C, D. Reservoir B is desirably charged with a solution of the selected air-entraining agent in combination with the same solvent present in reservoir A. Generation of the absorbance curve for the contents of reservoir B is used to identify the air-entraining agent from its absorbance curve stored in memory from previous determinations, which also ascertains that the AEA being used is consistent with an absorbance curve for the same AEA previously determined and stored in memory. Reservoir C is charged with a solution of fly ash in combination with the solvent of Reservoir A. Prior to charging reservoir C, the mixture of fly ash and solvent is agitated well and solids are filtered out. The absorbance curve derived from Reservoir C is considered as being a reference absorbance curve for the contents of reservoir D. Reservoir D is charged with a mixture comprising the fly ash selected, the air-entraining agent, and the solvent. After these are combined, they are mixed well and filtered to remove solids as earlier described herein, prior to charging into reservoir D.

One advantage of system 10 and the methods herein is that background noise is eliminated by alternatively employing and taking data readings on the reference material, which in some embodiments is the ultra pure water. However, it is not necessary that ultra-pure water be employed, since the system by its subtraction methodology of the relative spectra obtained automatically corrects for any impurities in the solvent. The overall result is that the system exhibits a high signal-to-noise ratio superior to instruments according to the current state-of-the-art.

While described with reference to fly ash, the teachings of the present disclosure are equally applicable and useful with respect to powdered activated carbon, graphite, amorphous carbons and essentially any form of carbon having substantial sp2-hybridized character sufficient to absorb an AEA, when used or intended for use in a cement composition.

Consideration must be given to the fact that although this invention has been described and disclosed in relation to certain embodiments, equivalent modifications and alterations thereof may become apparent to persons of ordinary skill in this art after reading and understanding the teachings of this specification, drawings, and the claims appended hereto. The present disclosure includes subject matter defined by any combinations of any one or more of the features provided in this disclosure with any one or more of any other features provided in this disclosure. These combinations include the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. These combinations also include combination of the features and/or limitations of one or more of the independent claims with features and/or limitations of another independent claims to arrive at a modified independent claim, with the remaining dependent claims in their original text or as modified per the foregoing, being read and applied to any independent claim so modified. The present disclosure embraces modifications and alterations which achieve substantially the same result as herein taught using substantially the same or similar structures and materials, and the claimed invention shall be interpreted as encompassing subject matter commensurate with the broadest reasonable interpretation this disclosure provides a person of ordinary skill in this art after having the benefit of reading this disclosure.

What is claimed is:

1. A method for determining the relative quantities of air-entraining agent and fly ash material to be added to a cement composition, comprising:
    a) selecting an air-entraining agent to be used in formulating a cement composition;
    b) selecting a fly ash material to be used in formulating a cement composition;
    c) making a determination of the adsorption capacity of said selected air-entraining agent on said selected fly ash material; and
    d) calculating the relative quantities of air-entraining agent and fly ash material to be added to a cement composition based on said determination, wherein said determination is made by:
      i) generating an absorbance plot for said pre-selected solvent;
      ii) generating an absorbance vs. concentration plot for known concentrations of said air-entraining agent in a pre-selected solvent;
      iii) combining a known amount of said fly ash material and said solvent, to provide a first mixture, filtering said first mixture, and measuring the absorbance of said first mixture;
      iv) combining the same known amounts of said fly ash material and solvent as in step iii) above, and further including said air-entraining agent, to provide a second mixture, filtering said second mixture, and measuring the absorbance of said second mixture;
      v) taking the difference between the absorbance value of said filtered fly ash solution from step iii) above, and the absorbance value of said mixture of said air-entraining agent in combination with said filtered fly ash material from step iv) above; and
      vi) converting said difference from step v) to a numerical value representing the amount of said air-entraining agent adsorbed by said fly ash material, on a weight-to-weight basis.

2. A method according to claim 1 wherein the air-entraining agent is selected from the group consisting of: nonyl-phenol alkoxylates and alpha-olefin sulfonates.

3. A method according to claim 1 wherein said fly ash material is a by-product of the combustion of any selected fossil fuel.

4. A method according to claim 1 wherein the absorbance measurements are carried out in a test cavity comprising an optically transparent cuvette having greater than 95% transmission in the UV/Visible spectral range.

5. A method according to claim 1 wherein the absorbance measurements are carried out using a broadband UV/Visible/NIR light source.

6. A method according to claim 5 wherein the cavity is coupled to a narrow-band UV, Vis, or NIR source.

7. A method according to claim 1, which is carried out on equipment comprising:
    a) a plurality of liquid dispensers each having an inlet and an outlet;
    b) a switching valve having a plurality of inlet ports and an outlet port, said outlet of each of said dispensers being fluidly-connected to separate inlet ports present on said switching valve, said outlet port of said switching valve being configured to deliver a liquid from any of said dispensers into a cavity;
    c) an energy source disposed to emit electromagnetic radiation into said cavity; and d) a sensor unit disposed in proximity to said cavity for receiving a transmitted portion of said electromagnetic energy, after said energy passes through said cavity.

8. A method according to claim 7 wherein said liquid dispensers each contain a liquid sample selected from the group consisting of: a reference solution, and a neat solvent, an air-entraining agent solution, a filtered fly ash solution in said solvent, and a filtered fly ash solution in said solvent that also contains said air entraining agent.

9. A method according to claim 7 wherein the switching valve is microprocessor controlled to alternate between admitting the contents of any selected sample dispenser and a dispenser containing a specific reference solution corresponding to the selected sample.

10. A method according to claim 7 wherein the cavity is an optically transparent cuvette with greater than 95% transmission in the UV/Visible spectral range.

11. A method according to claim 7 wherein said cavity further comprises built-in electrodes for electrical conductivity or resistivity measurements.

12. A method according to claim 7 wherein a broadband UV/Visible/near-infrared light source is present and disposed to emit light into said cavity.

13. A method according to claim 7 wherein a narrow band UV/Visible/near-infrared light source is present and disposed to emit light into said cavity.

14. A method according to claim 11 wherein the cavity electrodes are connected to a voltage or current detector.

15. A method according to claim 7 wherein said electromagnetic radiation including light is conveyed from said cavity to a UV/Vis spectrometer.

16. A method according to claim 7 wherein said electromagnetic radiation including light is conveyed from said cavity to a photodetector.

17. Method for determining adsorption capacity of fly ash for any selected air entraining agent, said method comprising the steps of:
   a) providing a plurality of mixtures of said air-entraining agent in a solvent, said plurality of mixtures each having a different concentration of said air-entraining agent from one another;
   b) providing a source of said solvent that is free from said air-entraining agent;
   c) providing an energy source;
   d) providing a detector which outputs a signal responsive to intensity of said energy source, said detector being disposed sufficiently to receive energy from said energy source;
   e) imposing a first mixture between said energy source and said detector such that some of said energy passes through said first mixture during its travel from said energy source to said detector;
   f) recording a first signal from said detector;
   g) imposing said solvent that is free from said air-entraining agent between said energy source and said detector such that some of said energy passes through said solvent that is free from said air-entraining agent during its travel from said energy source to said detector;
   h) recording a second signal from said detector;
   i) subtracting said first signal from said second signal to provide a result;
   j) repeating each of steps e) through i) for each mixture of said plurality of mixtures;
   k) generating a data plot graph comprising each result to provide a graph of intensity versus concentration of said air-entraining agent in said solvent;
   l) providing a test mixture of a known amount of said air-entraining agent in said solvent;
   m) adding a known amount of a fly ash sample to said test mixture to provide a test aliquot;
   n) agitating said test aliquot sufficiently to cause said fly ash to adsorb said air entraining agent present in said test mixture substantially to the maximum capacity of said fly ash to adsorb said air entraining agent;
   o) imposing said test aliquot between said energy source and said detector such that some of said energy passes through said test aliquot during its travel from said energy source to said detector;
   p) recording the signal from said detector from step o);
   q) determining the concentration of air entraining agent present in said test aliquot by comparison to said data plot graph;
   r) subtracting the amount of air entraining agent present in said test aliquot after step n) from the amount originally present in said test aliquot prior to addition of said fly ash to determine the amount of air entraining agent was adsorbed by said fly ash;
   s) calculating the amount of air entraining agent adsorbed by said fly ash on a weight basis of air entraining agent mass to fly ash mass.

\* \* \* \* \*